(12) United States Patent
Poss et al.

(10) Patent No.: US 9,867,809 B2
(45) Date of Patent: Jan. 16, 2018

(54) ENCAPSULATED ACTIVE INGREDIENTS FOR CONTROLLED ENTERIC RELEASE

(71) Applicant: Kemin Industries, Inc., Des Moines, IA (US)

(72) Inventors: Mitchell Poss, Johnston, IA (US); Thoai Pham, Altoona, IA (US); David Sanders, Clive, IA (US); Jon Rubach, West Des Moines, IA (US); Shulin Feng, West Des Moines, IA (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 15/198,775

(22) Filed: Jun. 30, 2016

(65) Prior Publication Data

US 2017/0000736 A1    Jan. 5, 2017

Related U.S. Application Data

(60) Provisional application No. 62/186,787, filed on Jun. 30, 2015.

(51) Int. Cl.
*A61K 9/14* (2006.01)
*A61K 31/19* (2006.01)
(Continued)

(52) U.S. Cl.
CPC ........ *A61K 31/4172* (2013.01); *A61K 9/0056* (2013.01); *A61K 9/1611* (2013.01);
(Continued)

(58) Field of Classification Search
CPC .... A61K 31/00; A61K 31/19; A61K 31/4172; A61K 9/0056; A61K 9/1611; A61K 9/1617; A61K 9/1623; A61K 9/1694
See application file for complete search history.

(56) References Cited

U.S. PATENT DOCUMENTS

| | | | |
|---|---|---|---|
| 4,804,547 A | 2/1989 | Vanderbilt et al. |
| 5,591,878 A | 1/1997 | Nelson et al. |
| 5,707,646 A | 1/1998 | Yajima et al. |
| 7,550,504 B2 | 6/2009 | Pablos |
| 7,887,844 B2 | 2/2011 | Appel et al. |
| 8,603,538 B2 | 12/2013 | Lorenzon |

(Continued)

FOREIGN PATENT DOCUMENTS

| | | |
|---|---|---|
| CN | 1775064 | 12/2005 |
| EP | 0233819 | 1/1992 |

(Continued)

OTHER PUBLICATIONS

Chintharlapalli et al., "2-Cyano-3,12-dioxoolean-1,9-dien-28-oic Acid and Related Compounds Inhibit Growth of Colon Cancer Cells through Peroxisome Proliferator-Activated Receptor g-Dependent and -Independent Pathways", "Molecular Pharmacology", Jan. 24, 2005, pp. 119-128, vol. 68, No. 1, Publisher: Aspet.

(Continued)

*Primary Examiner* — Savitha Rao
(74) *Attorney, Agent, or Firm* — Nyemaster Goode P.C.

(57) ABSTRACT

A method of forming a granule having an internal three-dimensional framework of channels to control and sustain the release of an active ingredient for enteric delivery of the active ingredient in an animal fed the granule. In the composition of the granules hydrogenated vegetable oil, HVO for example, is combined with a modifier to create a granule with channels through which the active ingredient is released. The active ingredients, including but not limited to metal salts of butyric acid, can be released in the lower gut of the animal where it will best benefit the animal. By adjusting the amount of the modifier, the release rate of the active can be adjusted to suit the passage rate of the species of animal being fed.

5 Claims, 4 Drawing Sheets

(51) Int. Cl.
*A61K 31/4172* (2006.01)
*A61K 31/00* (2006.01)
*A61K 9/00* (2006.01)
*A61K 9/16* (2006.01)

(52) U.S. Cl.
CPC .......... *A61K 9/1617* (2013.01); *A61K 9/1623* (2013.01); *A61K 9/1694* (2013.01); *A61K 31/00* (2013.01); *A61K 31/19* (2013.01)

(56) References Cited

U.S. PATENT DOCUMENTS

| | | |
|---|---|---|
| 2004/0009206 A1 | 1/2004 | Piva et al. |
| 2007/0190177 A1 | 8/2007 | Kling et al. |
| 2011/0311634 A1 | 12/2011 | Goethals |
| 2013/0034629 A1 | 2/2013 | Goethals |
| 2014/0037698 A1 | 2/2014 | Pablos Perez |

FOREIGN PATENT DOCUMENTS

| | | |
|---|---|---|
| EP | 1439160 | 7/2004 |
| EP | 2373181 | 12/2008 |
| EP | 2025243 | 2/2009 |
| EP | 2727472 | 5/2014 |
| GB | 2466041 | 6/2010 |
| WO | 2008017659 | 2/2008 |
| WO | 2010066397 | 6/2010 |
| WO | WO2011/128871 | 10/2011 |

OTHER PUBLICATIONS

Wu et al., "Alternative Splicing Regulated by Butyrate in Bovine Epithelial Cells", "PLOS One", Jun. 1, 2012, vol. 7, No. 6, Publisher: Open Access.

Vanhoutvin et al., "Butyrate-Induced Transcriptional Changes in Human Colonic Mucosa", "PLOS One", Aug. 1, 2009, vol. 4, No. 8, Publisher: Open Access.

Nepelska et al., "Butyrate Produced by Commensal Bacteria Potentiates Phorbol Esters Induced AP-1 Response in Human Intestinal Epithelial Cells", "PLOS One", Dec. 1, 2012, vol. 7, No. 12, Publisher: Open Access.

Lin et al., "Butyrate and Propionate Protect against Diet-Induced Obesity and Regulate Gut Hormones via Free Fatty Acid Receptor 3-Independent Mechanisms", "PLOS One", Apr. 1, 2012, vol. 7, No. 4, Publisher: Open Access.

Dalmasso et al., "Butyrate Transcriptionally Enhances Peptide Transporter PepT1 Expression and Activity", "PLOS One", Jun. 1, 2008, vol. 3, No. 6, Publisher: Open Access.

Lim et al., "D-b-Hydroxybutyrate Is Protective in Mouse Models of Huntingtons Disease", "PLOS One", Sep. 1, 2011, vol. 6, No. 9, Publisher: Open Access.

Raso et al., "Effects of sodim butyrate and its synthetic amide derivative on liver infalmmation and glucose tolerance in an animal model of steatosis induced by high fat diet", "PLOS One", Jul. 1, 2013, p. 7, No. 8, Publisher: Open Access.

Mercado et al., "PLOS One", Nov. 1, 2013, vol. 8, No. 11, Publisher: Open Access.

Donohoe et al, "Microbial Regulation of Glucose Metabolism and Cell-Cycle Progression in Mammalian Colonocytes", "PLOS One", Sep. 1, 2012, vol. 7, No. 9, Publisher: Open Access.

Drago et al., "Propolis Augments Apoptosis Induced by Butyrate via Targeting Cell Survival Pathways", "PLOS One", Sep. 1, 2013, vol. 8, No. 9, Publisher: Open Access.

Cohen et al., "Zinc Sensing Receptor Signaling, Mediated by GPR39, Reduces Butyrate-Induced Cell Death in HT29 Colonocytes via Upregulation of Clusterin", "PLOS One", Apr. 1, 2012, vol. 7, No. 4, Publisher: Open Access.

Sigma-Aldrich Corporation, "Safety Data Sheet Poloxamer 407", "http://www.sigmaaldrich.com/SMDS/MSDS/DisplayMSDS", Jan. 28, 2015.

ENCAPSULATED ACTIVE INGREDIENTS FOR CONTROLLED ENTERIC RELEASE

RELATED APPLICATIONS

This application claims priority to U.S. Patent Application Ser. No. 62/186,787, filed Jun. 30, 2015, the entirety of which is included in this application by this reference.

BACKGROUND OF THE INVENTION

The present invention relates generally to animal feed supplements and, more specifically, to active ingredients, including metal butyric acid salts, micro-encapsulated in a three-dimensional matrix of modified fat to form a granule or beadlet that provides for controlled and sustained release of the metal butyric acid salts upon ingestion by an animal.

The efficacy and adsorption of a bioactive molecule in the digestive system is dependent on many different factors and properties of the molecule. To obtain the highest level of efficacy from the least amount of active ingredient in a formulation it is important to deliver the active molecules to the desired location in the digestive system over a specified period of time so as to provide the active ingredient through a timed and controlled release mechanism.

As an energy source, butyric acid can be taken up by the cells lining the gastrointestinal tract and used directly for energy. When butyric acid is used as a feed additive for production animals, it is quickly adsorbed and metabolized by the epithelial cells in the upper part of the digestive system, including the esophagus and stomach, and very little makes it to the small intestine and none of it can be utilized by the hind gut. Encapsulation can aid in the delivery of metal butyric acid salts to the small intestine where it has the most benefit to the animal. One common way of encapsulating metal butyric acid salts and other feed ingredients for sustained release is to embed the active ingredient in a solid fat matrix. The release rate of the active ingredient from the encapsulating material can vary, depending on the ingredient being encapsulated, the properties of the fat that is being used for the encapsulation, the 3D structure of the final encapsulated matrix, and the encapsulation processing conditions.

Zinc is an essential trace mineral that is necessary for the normal growth and performance of animals and human beings. Zinc has been shown to either increase the catalytic activity or contribute to structural stability, for more than 300 enzymes. Zinc is essential for calcification of the bone and for normal functioning of many hormones including thyroid and insulin. In simple terms, zinc seems to affect most of the biological functions either directly or indirectly. Apart from these basic functions recent studies indicate that zinc has the potential to influence immune function and also has beneficial effects towards intestinal health. Zinc is usually supplemented as zinc sulfate in animal diets but other forms of zinc is also available including zinc propionate, zinc oxide and zinc-amino acid combinations. Beneficial effects of these alternative combinations of zinc are inconclusive.

SUMMARY OF THE INVENTION

The present invention includes the encapsulation or coating of metal butyric acid salts, namely zinc, sodium, potassium, calcium, magnesium, iron, copper, chromium, manganese, or any other minerals in a modified fat matrix to create a spherical granule (approximately 0.1 to 2.0 mm in diameter and more optimally 0.5 to 1.2 mm in diameter). The granules have an internal three-dimensional (3D) structure consisting of channels originating from the interior of the granules and terminating at the granule surface which allows for a controlled and sustained release of the active ingredient through the dissolution of the porous structure. The active ingredient present in the granules may be at 1 to 70 wt %.

The present invention is directed to the use of a group of compounds/reagents for controlling the release of feed additive, nutritional, and/or pharmaceutical ingredients from hydrogenated vegetable oil (HVO), including preferably hydrogenated palm oil (HPO), or other high melting fat or wax micro bead encapsulations generated with spray freeze technology or other similar technologies. Due to the chemical property of the active ingredients and unique characteristics of gut physiology for humans and other animals, targeted delivery and controlled release of the active ingredients is required for optimal efficacy. In poultry for example, the retention time of feed in the gut is relatively short and there is a need for rapid or faster release of the active ingredient to the gut from the encapsulation. In a bovine (ruminant), on the other hand, a slower release is required to allow for the targeted delivery of the active ingredient in the hindgut. In addition, due to the high acid level in the stomach, active ingredients may have to be protected from degradation to be released in the small intestine. Active ingredients have to be released at the right time and at the right location to be efficacious. There have been reports and practices of using HPO or high melting fat for encapsulation of active ingredients, but there have been no reports of methodologies to modify the characteristics of the fat matrix to control the release of actives with this encapsulation system. In the current invention propylene glycol, tween-20, polyethylene glycol, water, aqueous salt solutions, aqueous potassium hydroxide solution, and other polar compounds that are liquid under ambient temperatures and polar powder compounds, such as amino acids, salts and the like, that do not mix well with fat, were used at different concentrations to either increase or decrease the release of active ingredients from encapsulation. When these compounds were included one at a time or in combination, the release of active ingredients from the encapsulation beads was modified. The more modifiers included, the faster the release. The lower the amount of modifiers included, the slower the release. This was demonstrated with ZBA (the zinc salt of butyric acid in a molar ratio of 1:2) as the encapsulated active ingredient but would apply to other feed additives, nutritional and pharmaceutical active ingredients as well.

In a preferred embodiment, the active ingredient is ZBA containing zinc and butyric acid, a short chain fatty acid with many biological functions in the gastrointestinal tract of animals. The present invention improves the release of ZBA in animals, as shown in the improved growth of animals and the improved bioavailability of the butyric acid in the small intestine.

DESCRIPTION OF THE INVENTION

Figure 1:
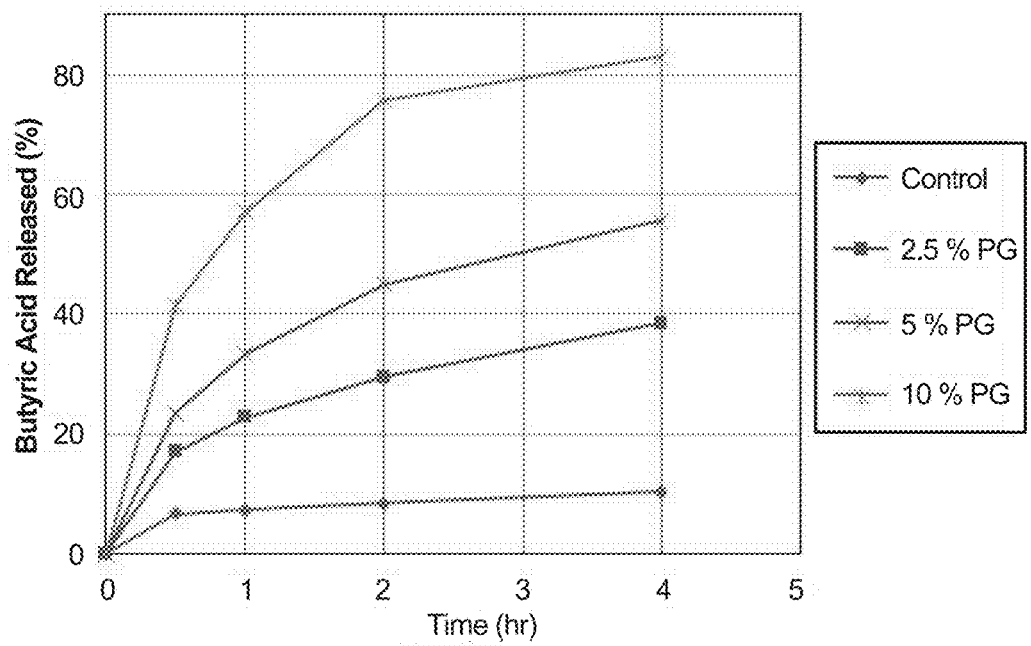
FIG. 1 is a chart of the effect of propylene glycol concentration on dissolution as indicated by butyric acid released.

The present invention includes a method of forming a granule having an internal three-dimensional framework of channels to control the rate of release of an active ingredient from the granule. The method includes melting a vegetable oil, mixing into the melted vegetable oil a selected amount of at least one modifier and a selected amount of at least one active ingredient to form a melt composition, forming droplets of the melt composition and cooling the droplets to form a granule having an internal three-dimensional framework of channels. The modifiers are selected from compositions including but not limited to glycerine, Tween 20, Tween 80, propylene glycol, sodium stearate, lecithin, ionic and non-ionic surfactants, potash, aqueous potash and polyethylene glycol.

In preferred embodiments of the present invention, the selected amount of total modifiers is between 0.1 wt % and 20 wt % and all values between such limits, including, for example, without limitation or exception, the selected amount of total modifiers may be 0.2 wt %, 0.69 wt %, 3.47 wt %, 12.4 wt % and 19.99%. Stated another way, in preferred embodiments of the invention, the modifiers can take any value "ab.cd" wt % wherein a is selected from the numerals 0, 1 and 2, and b, c and d are each individually selected from the numerals 0, 1, 2, 3, 4, 5, 6, 7, 8 and 9, with the exception that c cannot be less than 1 if a, b and d are all 0 and b, c and d are all 0 if a is 2.

In preferred embodiments of the present invention, the selected amount of total active ingredients is between 1 wt % and 70 wt % and all values between such limits, including, for example, without limitation or exception, the selected amount of total modifiers may be 2 wt %, 13.45 wt %, 55.5 wt %, 62.11 wt % and 69.9%. Stated another way, in preferred embodiments of the invention, the modifiers can take any value "ab.cd" wt % wherein a is selected from the numerals 0, 1, 2, 3, 4, 5, 6 and 7, and b, c and d are each individually selected from the numerals 0, 1, 2, 3, 4, 5, 6, 7, 8 and 9, with the exception that c cannot be less than 1 if a, b and d are all 0 and b, c and d are all 0 if a is 7.

EXAMPLE 1

Modifier Screening.

Compounds that were tested as potential modifiers of a fat matrix to obtain a self-supporting 3D-structure suitable for the controlled release of ZBA are listed in Table 1. These compounds were individually formulated at specific level with the hydrogenated vegetable oil and ZBA to generate encapsulated prototypes. The granules were formed by heating and stirring the composition until it melted and then applying the composition onto a spinning disc assembly. The spinning disc generates the droplets within a chamber flooded with a cloud of liquid nitrogen, resulting in a solidified droplet that was collected at the bottom of the chamber. Granules ranged from 0.1 mm to 2 mm diameter were collected. Prototypes with different formulations were then tested for butyric acid release in a shaker bath dissolution assay. Based on dissolution, the modifier that allowed for the formation of granules having suitable size, integrity, and shelf life while also provided for controlled and sustained release was propylene glycol, at a concentrations ranging from 1% to 20% in the final formula.

TABLE 1

Formulations designed to screen for modifiers.

| Granule Size | Test # | Sample | Modifier | ZBA[1] (%) | HPO[2] (%) | Modifier Concentration (%) | 4 Hours Dissolution (%) |
|---|---|---|---|---|---|---|---|
| Micro (5 μL) | 3 | Control | — | 40 | 60 | 0 | 9.84 |
| | 3 | 3A | Glycerin | 40 | 55 | 5 | ** |
| | 3 | 3B | Lecithin | 40 | 55 | 5 | 1.52 |
| | 3 | 3C | Tween20 | 40 | 55 | 5 | ** |
| | 3 | 3D | Tween80 | 40 | 55 | 5 | 34.84 |
| | 4 | Control | — | 40 | 60 | 0 | 10.27 |
| | 4 | 4A | Glycerin | 40 | 57.5 | 2.5 | ** |
| | 4 | 4B | 1% Glycerin + 1% Lecithin | 40 | 58 | 2 | 2.87 |
| Mini (25 μL) | 5 | Control | — | 50 | 50 | 0 | 5.85 |
| | 5 | 5A | Propylene Glycol | 50 | 47.5 | 2.5 | 12.31 |
| | 5 | 5B | Propylene Glycol | 40 | 54.7 | 5.3 | 23.44 |
| | 5 | 5C | Sodium Stearate | 50 | 47.5 | 2.5 | 4.56 |
| | 6 | 6A | Propylene Glycol | 40 | 50 | 10 | 18.75 |
| | 6 | 6B | Propylene Glycol* | 40 | 50 | 10 | 32.08 |
| | 6 | 6C | Polyethylene Glycol | 40 | 50 | 10 | 34.11 |
| | 6 | 6D | Polyethylene Glycol* | 40 | 50 | 10 | 36.79 |
| | 7 | Control | — | 40 | 60 | 0 | 3.92 |
| | 7 | 7A | Propylene Glycol | 40 | 59 | 1 | 5.43 |
| | 7 | 7B | Propylene Glycol | 40 | 58 | 2 | 15.10 |
| | 7 | 7C | Propylene Glycol | 40 | 57 | 3 | 19.28 |
| | 7 | 7D | Propylene Glycol | 40 | 56 | 4 | 23.87 |
| | 7 | 7E | Propylene Glycol | 40 | 55 | 5 | 22.08 |
| | 8 | Control | — | 40 | 60 | 0 | 4.82 |
| | 8 | 8A | Propylene Glycol | 40 | 50 | 10 | 37.97 |

TABLE 1-continued

Formulations designed to screen for modifiers.

| Granule Size | Test # | Sample | Modifier | ZBA[1] (%) | HPO[2] (%) | Modifier Concentration (%) | 4 Hours Dissolution (%) |
|---|---|---|---|---|---|---|---|
| | 8 | 8B | Propylene Glycol | 40 | 45 | 15 | 47.50 |
| | 9 | Control | Propylene Glycol | 40 | 57.5 | 2.5 | 16.54 |
| | 9 | 9A | Propylene Glycol + 0.5% NaHCO$_3$ | 40 | 57 | 3 | 19.37 |
| Mega (50 μL) | 1 | Control | — | 40 | 60 | 0 | 2.78 |
| | 1 | Sugar | 49.20% sucrose in water | 40 | 56 | 4 | 1.44 |
| | 2 | 2A | Glycerin | 40 | 57.5 | 2.5 | 2.66 |
| | 2 | 2B | Glycerin | 40 | 57.5 | 2.5 | 2.51 |
| | 2 | 2C | Glycerin | 40 | 57.5 | 2.5 | 2.77 |
| | 2 | Control | — | 40 | 60 | 0 | 2.44 |

*Mixed with ZBA first then with hydrogenated palm oil
** Mixture was too viscous to make granules.
[1]ZBA = The salt of zinc and butyric acid in a ratio of 1:2.
[2]HPO = Hydrogenated palm oil.

Dissolution Testing.

Dissolution was conducted with a mechanical shaking water bath that was loaded with individual flask for each sample. 0.5 grams of granules was weighed into a 125 mL Erlenmeyer flask containing 70 mL deionized water at 37° C. The flask was agitated in a 37±2° C. shaking bath for 4 hours. A 0.5 mL aliquot of solution was collected at 0.5, 1, 2, and 4 hours interval for gas chromatography analysis to determine the amount of butyric acid released at each time point. Dissolution percentage at each time point was determined by dividing the amount of butyric acid in solution at that specific time point with the amount of total butyric acid in the granule.

Particle Size Analysis.

20-30 g of pearls was analyzed on a Malvern Mastersizer 2000. Particle size distribution was determined with laser diffraction technique by measuring the intensity of light scattering as a laser beam passes through a dispersed particulate sample.

Gas Chromatography (GC) Analysis.

0.5 mL aliquot of dissolution solution was loaded into a GC vial containing 1 mL of 500 ppm valeric acid in 1N HCl. The total of 1.5 mL solution in the GC vial was mixed and analyzed on a gas chromatograph.

Effect of Propylene Glycol (PG) on Dissolution.

Four different encapsulated prototypes were produced to make a product of encapsulated ZBA (EZBA) with HPO. For the control mixture, only ZBA and HPO were in the mixture. To test the effect of propylene glycol on dissolution, 2.5%, 5.0% and 10.0% of propylene glycol was included for making the encapsulates S1, S2, and S3 respectively. Gram quantities of encapsulated prototypes were then made for the initial production utilizing spray-freeze tower/technology. The dissolution results for these encapsulated prototypes are listed in Table 3. As the concentration of propylene glycol (PG) is increased, the dissolution rate increased, allowing for PG dose dependent control of dissolution rate. Sample S1 with 2.5% of propylene glycol had dissolution of 38.63%, and sample S3 with 10% propylene glycol had dissolution rate of 83%, representing the percent of total butyric acid released within 4 hours (FIG. 1).

TABLE 3

Dissolution of granules with different concentration of propylene glycol.

| Sample | ZBA (%) | Hydrogenated Vegetable Oil (%) | Propylene glycol (%) | Dissolution Time | | | |
|---|---|---|---|---|---|---|---|
| | | | | 0.5 h (%) | 1 h (%) | 2 h (%) | 4 h (%) |
| Control | 40 | 60.0 | 0 | 6.67 | 7.46 | 8.53 | 10.43 |
| S1 | 40 | 57.5 | 2.5 | 17.10 | 22.86 | 29.51 | 38.63 |
| S2 | 40 | 55.0 | 5.0 | 23.60 | 33.53 | 44.94 | 55.79 |
| S3 | 40 | 50.0 | 10.0 | 41.47 | 57.33 | 75.67 | 83.12 |

Figure 2A:
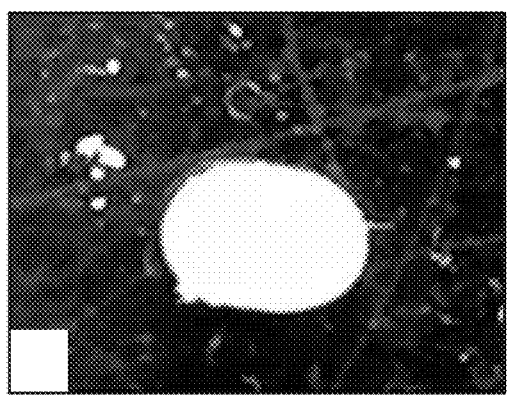
FIGS. 2A and 2B are photographs showing a cross section of granules from micro-channel test; panel A shows an unmodified granule in red dye solution overnight before cut open, panel B shows a modified, PG-treated granule in red dye solution overnight before cut open.
Figure 2B:
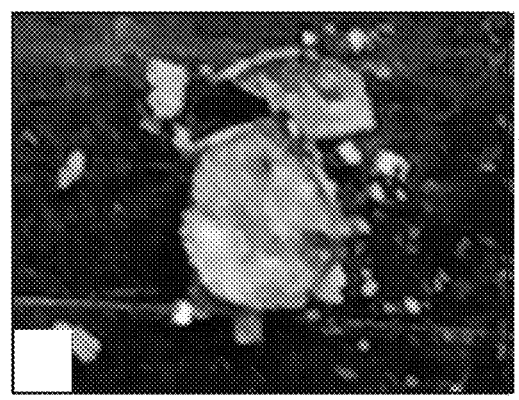

To determine the effect of propylene glycol on the structure of the encapsulation granules, tests were conducted to examine the penetration of a red dye into the interior of the encapsulated granules. Formulations of both control and fast release granules were soaked in a red dye solution for 16 hours. The granules were then broken open to expose the cores. FIG. 2 shows that the propylene glycol in the formulation produces micro-channels that allow the dye to penetrate and for the encapsulated active to dissolve. The control granule did not take up any of the dye and therefore does not have the micro-porous structure.

EXAMPLE 2

Performance Trial in Broiler Chickens

A chicken, broiler performance trial was completed to understand if granules with different in-vitro dissolution rates would perform differently in an animal model. In a typical, broiler the passage rate is 2-6 hours through the gut and a fast release mechanism is needed such that the majority of the active ingredient is released in the hind gut. Therefore two different granules were made, one with a fast dissolution, and one with a slow dissolution. The controls did not contain any active ingredients, while the other treatment groups included the ZBA powder treatment, ZBA slow release granules treatment, and ZBA fast release granule treatment. The experiment used 72 cages of 10 male Cobb×Cobb 500 broiler chickens. The treatments were replicated in eighteen blocks where the four treatments were randomized within each block.

Encapsulated ZBA formulations used in the animal trial:
Slow Release Formula
   40% ZBA
   60% HPO
Fast Release Formula
   40% ZBA
   57.5% HPO
   2.5% Propylene Glycol

TABLE 4

Treatments used in the performance trial.

| Treatments | Treatment Details | Amount of supplement added in Treatment | Amount of supplemental zinc added | Amount of butyric acid added |
| --- | --- | --- | --- | --- |
| 1. Negative Control | Basal Diet + ZnSO₄ | 0.69 kg/MT | 153 ppm | — |
| 2. ZBA Powder | Basal Diet + Zinc and Butyric Acid Salt Powder | 0.56 kg/MT | 153 ppm | 407 ppm |
| 3. Slow Release ZBA Granule | Basal Diet + Slow Release Granule | 1.4 kg/MT | 153 ppm | 407 ppm |
| 4. Fast Release ZBA Granule | Basal Diet + Fast Release Granule | 1.4 kg/MT | 153 ppm | 407 ppm |

All the treatments contained equal amount of zinc and treatments B, C and D had same amount of butyric acid. The diet given in Tables 5 and 6 was supplemented with the treatments in Table 4. The starter diet was fed day 0 to 14 and the grower diet was fed day 14 to 28. All diets were fed as non-pelleted mash feed.

TABLE 5

Diet formulation for starter and grower phases.

| Ingredient Name | Starter (0 to 14 d) % inclusion | Grower (14-28 d) % inclusion |
| --- | --- | --- |
| Corn, yellow, grain | 63.73 | 67.59 |
| Soybean meal dehulled, solvent | 26.28 | 22.6 |
| De-oiled DDGS (poet) | 4 | 4 |
| Fat, vegetable | 1.8 | 1.8 |
| Dicalcium phosphate. | 1.49 | 1.33 |
| Calcium carbonate | 1.02 | 1 |
| Salt, plain (NaCl) | 0.42 | 0.42 |
| Methionine MHA | 0.41 | 0.38 |
| L-Lysine | 0.52 | 0.53 |
| L-Threonine 98.5 | 0.17 | 0.18 |
| Trace Mineral | 0.08 | 0.08 |
| Vitamin premix | 0.07 | 0.07 |
| TiO2 marker | 0.4 | 0.4 |
| Ronozyme p-(ct) | 0.02 | 0.02 |

TABLE 6

Diet formulation for starter and grower phases.

| Nutrient Name | Starter (0 to 14 d) % inclusion | Grower (14-28 d) % inclusion |
| --- | --- | --- |
| Dry matter | 87.96 | 87.90 |
| Protein, crude | 19.72 | 18.26 |
| Fat, crude | 4.46 | 4.56 |
| Fiber, crude | 2.29 | 2.25 |
| Calcium | 0.90 | 0.85 |
| Phos. Total | 0.64 | 0.6 |
| Phos., available | 0.45 | 0.42 |
| M.e. Poultry | 3,000 | 3,040 |
| Methionine | 0.68 | 0.63 |
| Lysine | 1.4 | 1.32 |
| Tryptophan | 0.26 | 0.22 |
| Threonine | 0.94 | 0.88 |
| Sodium | 0.2 | 0.2 |
| Potassium | 0.73 | 0.67 |
| Chloride | 0.29 | 0.29 |
| dig methionine | 0.64 | 0.6 |
| dig cysteine | 0.27 | 0.25 |
| dig lysine | 1.28 | 1.2 |
| dig tryptophan | 0.23 | 0.21 |
| dig threonine | 0.82 | 0.77 |
| dig isoleucine | 0.83 | 0.75 |
| dig histidine | 0.48 | 0.44 |
| dig valine | 0.93 | 0.85 |
| dig leucine | 1.63 | 1.54 |
| dig arginine | 1.16 | 1.05 |
| dig phenylalanine | 0.95 | 0.87 |
| dig TSAA | 0.91 | 0.85 |

Bird weights and feed consumption by cage were recorded on Days 0, 14, 21, 28.

On days 14 and 28, after weighing, 4 birds per cage were harvested. From each of the harvested birds, a 1 inch section from the beginning of the ileum was cut off and flash frozen. The remaining intestinal tract was cut into 3 sections (upper, middle and cecal), the intestinal contents for each section were pooled by cage, and frozen in liquid nitrogen. A sample of excreta was collected by cage and frozen.

The samples of the feed and intestinal contents were analyzed for butyric acid by gas chromatography.

Results

Figure 3:
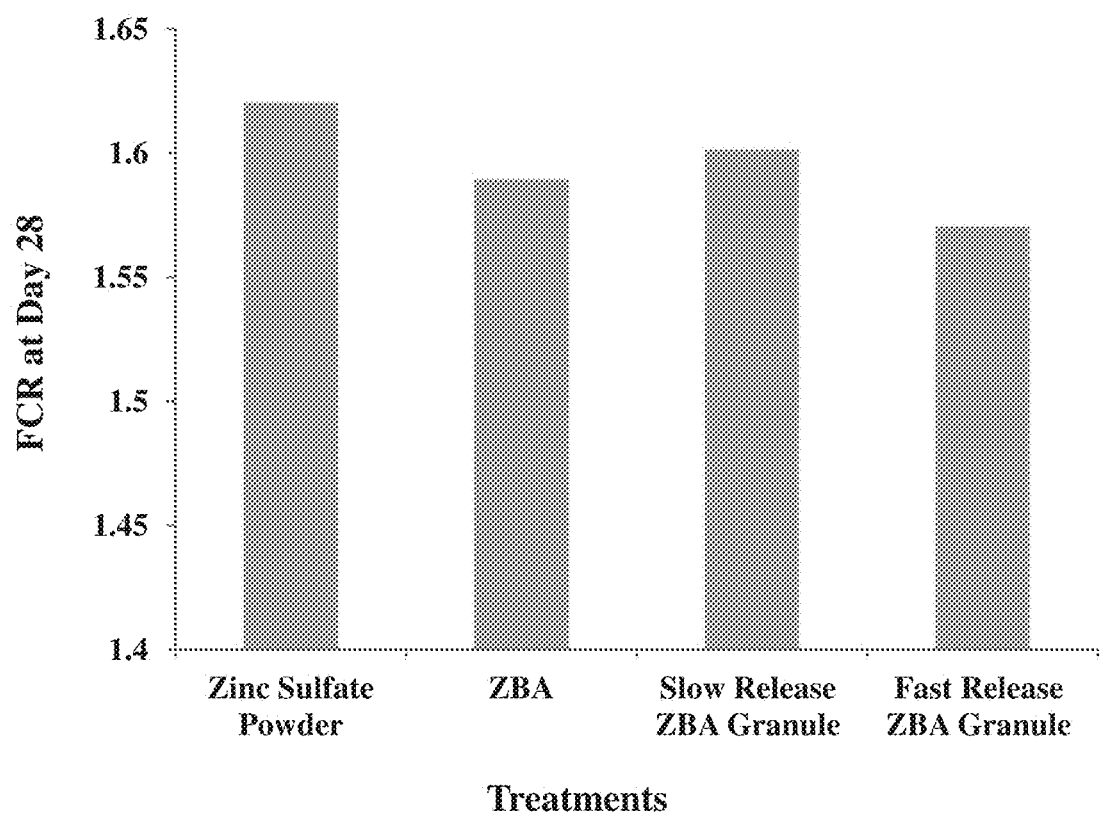
FIG. 3 is a chart of feed conversion at 28 days for the treatments with different formulations of ZBA encapsulation granules.

The performance results from the trial are shown in Table 7. Feeding the fast release granule to the birds resulted in better growth performance, as shown by the improvement in feed conversion (FIG. 3) and the improvement in weight gain after 28 days.

TABLE 7

Performance results after 28 days.

| Treatment | Feed Intake | Feed Conversion | Avg. Wt. (kg) |
| --- | --- | --- | --- |
| 1. Zinc Sulfate Powder | 10.93 | 1.620 | 1.010 |
| 2. ZBA Powder | 11.06 | 1.589 | 1.043 |
| 3. Slow Release Control Granule | 11.04 | 1.601 | 0.995 |
| 4. Fast Release Granule | 11.33 | 1.570 | 1.046 |

Figure 4:
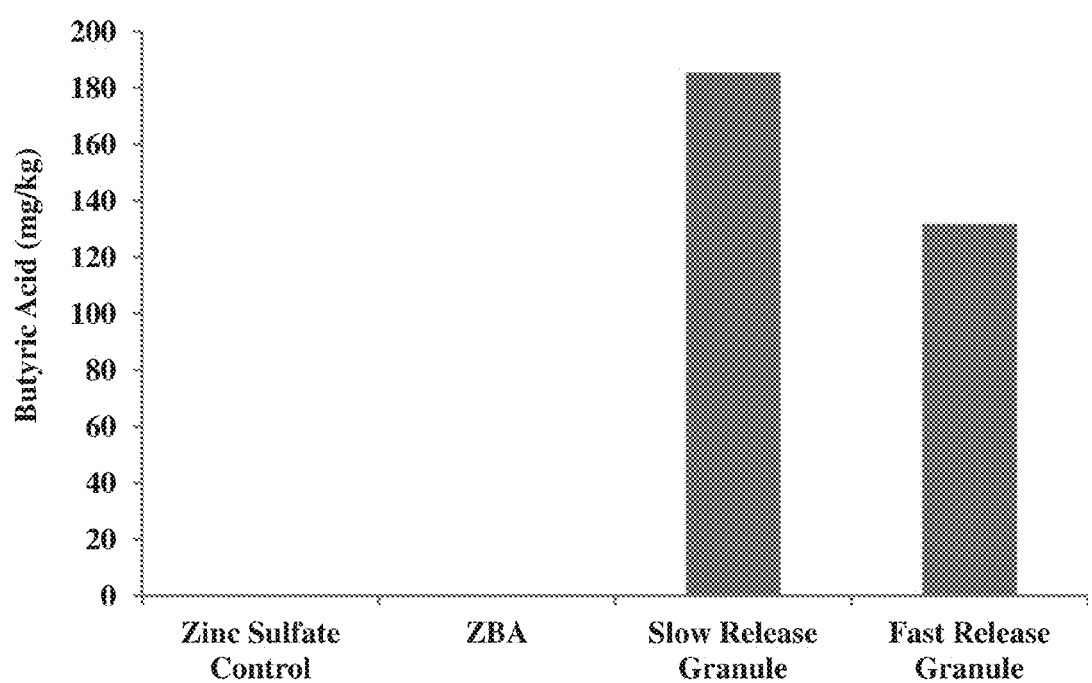
FIG. 4 is a chart of the butyric acid levels in the ileal contents of birds grown to 28 days.

From the intestinal contents collected at day 28, for the birds fed the control diet, or the ZBA in powder form, there was no detectible butyric acid in the ileal contents (FIG. 4). Indicating, the butyric acid is absorbed in the bird before it reaches the small intestine, and is not available in the small intestine, where it can enhance intestinal barrier function. The ileal contents of the birds fed the slow release granules or fast release granules have detectable levels of butyric acid. The birds fed the slow release granule diet had a higher amount of butyric acid in their intestinal contents as compared to the birds fed the fast release granules (FIG. 4). This is consistent with butyric acid still being inside the slow release granule and is therefore not providing the optimal benefits to the birds.

Figure 5:
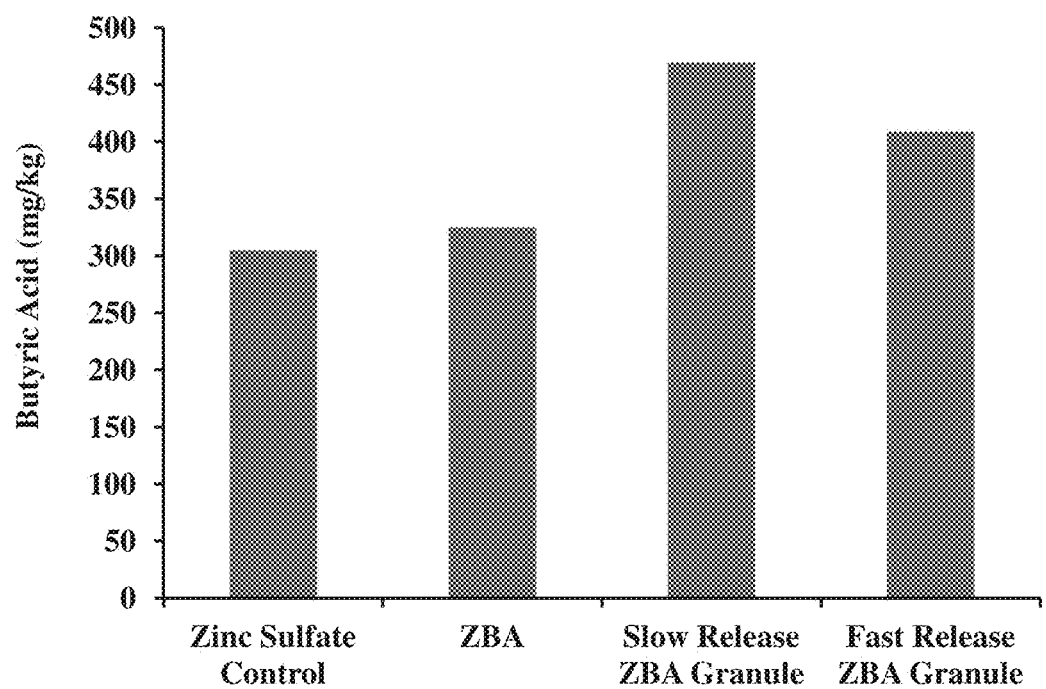
FIG. 5 is a chart of the butyric acid levels in the excreta of birds grown to 28 days.

The butyric acid levels in the day 28 excreta of the birds fed the diets containing the fast release granules are similar to that in the control treatment with no added butyric acid and the ZBA treatment, in which no butyric acid was detected in the jejunum. This illustrates that most of the butyric acid supplemented as fast release granules was released in the gut of the birds. The overall higher levels of butyric acid detected in the excreta are likely due to the fermentation by bacteria in the ceca and excreta of the birds. This means that the majority of the butyric acid being detected in the excreta is not the butyric acid that was added to the diet (FIG. 5).

Discussion

It is clear from the 28 day performance data that the best growth performance is obtained from the treatment that contains the fast release formulation of ZBA (Table 7). The fast release formulation allows for sustained release throughout the gastrointestinal tract of the animal (FIG. 4) and the excreta of the bird fed the fast release formulation does not contain more butyric acid than the excreta from the birds fed the control diet that does not have ZBA supplementation.

EXAMPLE 3—RELEASE OF HISTIDINE

Histidine encapsulation granules were prepared with a pilot encapsulation system as described generally in Example 1 to contain no propylene glycol and 50% histidine or 2% propylene glycol and 50% histidine. A United States pharmacopeia (USP) dissolution test was conducted to determine the release of histidine from the encapsulation granules. Briefly, 5 grams of granules was weighed into a Distek dissolution bowl containing 700 mL deionized water at 37° C. The mixture was stirred with a flat agitator blade at 100 rpm for 8 hours, with samples collected after 2, 4, 6, and 24 hours. The results indicated that propylene glycol significantly increased the release of histidine from its encapsulation granules from 20% to over 80% after 24 hours of dissolution, thus supporting the use of propylene glycol to modify the release of histidine from encapsulation.

EXAMPLE 4—RELEASE OF CBA

CBA (the salt of copper and butyric acid in a 1:2 molar ratio) encapsulation granules were prepared with a pilot encapsulation system as described generally in Example 1 and formulated to contain 50% CBA and 0 to 4% of propylene glycol with a pilot encapsulation system. The granules generated were tested for release of a salt of copper and butyric acid in a United States pharmacopeia (USP) dissolution assay. Briefly, 5 grams of granules was weighed into a Distek dissolution bowl containing 700 mL deionized water at 37° C. The mixture was stirred with a flat agitator blade at 100 rpm with samples collected after 1, 2, 4, and 8 hours. The results indicated that propylene glycol increased the release of the salt of copper and butyric acid in a dose dependent manner. The release was increased from 11% in the control granules to 35% in the granules with 4% propylene glycol after 8 hours of dissolution. It can be concluded that propylene glycol can be used to modify the release of ZBA from encapsulate.

EXAMPLE 5—RELEASE OF CBA

CBA encapsulation granules as described generally in Example 1 were formulated to contain from 0 to 2% of propylene glycol and CBA, which has a distinct blue color. The granules were placed in a dissolution apparatus for about 8 hours. By visual examination, propylene glycol formulated material had a shallower blue color and therefore increased the release of CBA in a dose dependent manner from encapsulate.

EXAMPLE 6—RELEASE OF ZBA

ZBA encapsulation granules as described generally in Example 1 were prepared in the laboratory. The granules were cut open and examined with scanning electronic microscopy (SEM). The analysis established that the granules contained propylene glycol were more porous than that without propylene glycol. Propylene glycol present in the granulation process helps form a unique three dimensional structure within the granules to facilitate the release of actives from encapsulates as evidenced by the microscopic observation of the gradual release of ZBA from the granules.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A method of forming a granule having an internal three-dimensional framework of channels to control the rate of release of an active ingredient from the granule, comprising:
   (a) melting a vegetable oil;
   (b) mixing into the melted vegetable oil a selected amount of at least one modifier and a selected amount of at least one active ingredient to form a melt composition;
   (c) forming droplets of the melt composition; and
   (d) cooling the droplets to form a granule having an internal three-dimensional framework of channels; wherein the at least one modifier is a polar compound that is a liquid at ambient temperature.

2. The method of claim 1, wherein the selected amount of said at least one modifier is changed to either increase or decrease the release rate of the active ingredient from the granule upon ingestion by an animal.

3. The method of claim 1 wherein the modifiers are selected from the group consisting of glycerine, Tween 20, Tween 80, propylene glycol, sodium stearate, lecithin, ionic and non-ionic surfactants, potash, aqueous potash and polyethylene glycol.

4. The method of claim 3 wherein the selected amount of total modifiers is between 0.1 and 20 percent by weight.

5. The method of claim 1, wherein the active ingredient is selected from the group consisting of metal salts of butyric acid, carotenoids and amino acids, and other compounds spanning from nutritional ingredients, pharmaceutical actives, flavor compounds, and coloration compounds.

* * * * *